(12) United States Patent
Aidun et al.

(10) Patent No.: US 8,927,287 B2
(45) Date of Patent: *Jan. 6, 2015

(54) METHOD FOR DISPERSION OF ASSEMBLIES OF BIOLOGICAL MATERIAL

(75) Inventors: Cyrus K. Aidun, Marietta, GA (US); Ulrika Egertsdotter, Marietta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 134 days.

This patent is subject to a terminal disclaimer.

(21) Appl. No.: 13/500,904

(22) PCT Filed: Oct. 7, 2010

(86) PCT No.: PCT/SE2010/051083

§ 371 (c)(1),
(2), (4) Date: Jun. 26, 2012

(87) PCT Pub. No.: WO2011/043731

PCT Pub. Date: Apr. 14, 2011

(65) Prior Publication Data

US 2012/0258536 A1    Oct. 11, 2012

Related U.S. Application Data

(60) Provisional application No. 61/250,021, filed on Oct. 9, 2009.

(30) Foreign Application Priority Data

Oct. 9, 2009    (SE) ...................................... 0950743

(51) Int. Cl.
*C12N 5/02*        (2006.01)
*A61B 17/43*    (2006.01)
*C12M 1/33*     (2006.01)

(52) U.S. Cl.
CPC .................................... *C12M 45/02* (2013.01)
USPC ............................................ 435/430; 600/33

(58) Field of Classification Search
CPC .......... C12M 45/02; C12M 1/33; C12M 1/42; C12M 47/06; C12N 1/06; C12N 5/04; C12N 2531/00; C02F 11/00; A01H 4/00; A01H 4/001

See application file for complete search history.

(56) References Cited

U.S. PATENT DOCUMENTS

| | | | |
|---|---|---|---|
| 4,146,468 A | 3/1979 | Wilson | |
| 4,959,158 A | 9/1990 | Meikrantz | |
| 5,284,765 A | 2/1994 | Bryan et al. | |
| 5,563,061 A | 10/1996 | Gupta | |
| 5,591,340 A | 1/1997 | Meikrantz et al. | |
| 5,821,116 A | 10/1998 | Herman | |
| 6,193,647 B1 * | 2/2001 | Beebe et al. ..................... | 600/33 |
| 6,684,564 B1 | 2/2004 | Hirahara | |
| 7,568,309 B2 | 8/2009 | Hirahara | |
| 8,394,633 B2 | 3/2013 | Aidun | |
| 2005/0246802 A1 | 11/2005 | Attree et al. | |
| 2008/0108137 A1 * | 5/2008 | Rigaut .......................... | 435/383 |

FOREIGN PATENT DOCUMENTS

| | | |
|---|---|---|
| CN | 101035426 A | 9/2007 |
| WO | 96/25484 A1 | 8/1996 |
| WO | 2009/029852 A2 | 3/2009 |
| WO | 2009/126757 A2 | 10/2009 |
| WO | 2009/126758 A1 | 10/2009 |
| WO | 2011/042888 A2 | 4/2011 |

OTHER PUBLICATIONS

Parsheh et al., "Variation of Fiber Orientation in Turbulent Flow Inside a Planar Contraction with Different Shapes", International Journal of Multiphase Flow, vol. 32, 2006, pp. 1354-1369.
International Search Report and Written Opinion received for PCT Patent Application No. PCT/SE2010/051083, mailed on Nov. 9, 2010, 12 pages.
Office Action received for Chinese Patent Application No. 201080045536.5, mailed on Mar. 15, 2013, 22 pages (13 pages of English Translation and 9 pages of Office Action).
International Preliminary Report on Patentability received for PCT Patent Application No. PCT/SE2010/051083, mailed on Apr. 19, 2012, 10 pages.
Examination Report received for New Zealand Patent Application No. 599717, mailed on Feb. 28, 2014, 2 pages.
Non-Final Office Action received for U.S. Appl. No. 13/500,886, mailed on May 22, 2014, 6 pages.
Office Action received for Chinese Patent Application No. 200980112745.4, issued on Dec. 29, 2011, 10 pages (6 pages of English Translation and 4 pages of Office Action).

(Continued)

*Primary Examiner* — Annette Para
(74) *Attorney, Agent, or Firm* — Morrison & Foerster LLP

(57) ABSTRACT

Methods and devices for dispersion of assemblies of biological material (such as plant embryogenic mass, plant tissue, cultured plant cells, animal tissue and/or cultured animal cells) suspended in a liquid are disclosed. The methods comprise i) subjecting the assemblies of biological material to fluid dynamics forces causing axially extensional strain and radially compressional strain and ii) subjecting the assemblies of biological material to fluid dynamics forces causing axially compressional strain and radially extensional strain fluid dynamics and iii) repeating said steps i) and ii) in sequence until assemblies of biological material is dispersed into the desired smaller size. The devices may comprise a flow channel arranged in a loop configuration for re-circulation in the flow channel, the flow channel including at least one constriction, such that the assemblies of biological material flowing through the flow channel are first subjected to axially extensional strain and radially compressional strain, and then to axially compressional strain and radially extensional strain from fluid dynamics forces.

5 Claims, 4 Drawing Sheets

(56) References Cited

OTHER PUBLICATIONS

Office Action received for Chinese Patent Application No. 2010880045552.4, mailed on Jul. 15, 2013, 15 pages (8 pages of English Translation and 7 pages of Office Action).
Extended European Search Report received for European Patent Application No. 10821666.4 mailed on Jun. 26, 2013, 6 pages.
European Search Report received for European Patent Application No. 10821666.4 mailed on Sep. 13, 2013, 8 pages.
International Preliminary Report on Patentability received for PCT Patent Application No. PCT/IB2010/054557, mailed on Apr. 19, 2012, 8 pages.
International Search Report and Written Opinion received for PCT Patent Application No. PCT/IB2010/054557, mailed on Apr. 22, 2011, 10 pages.
International Search Report received for PCT Patent Application No. PCT/US2009/039981, mailed on Sep. 30, 2009, 3 pages.
Written Opinion of the International Search Authority received for PCT Patent Application No. PCT/US2009/039981, mailed on Sep. 30, 2009, 4 pages.
International Preliminary Report on Patentability received for PCT Patent Application No. PCT/US2009/039981, completed on Mar. 22, 2010, 4 pages.
Office Action received for New Zealand Patent Application No. 599717, mailed on Dec. 4, 2012, 1 page.
Belmonte et al., "Alterations of the Glutathione Redox State Improve Apical Meristem Structure and Somatic Embryo Quality in White Spruce (Picea Glauca)", Journal of Experimental Botany, vol. 56, No. 419, Sep. 2005, pp. 2355-2364.
Greenspan et al., "On the Centrifugal Separation of a Bulk Mixture", International Journal of Multiphase Flow, vol. 11, No. 6, 1985, pp. 825-835.
Harrell et al., "Machine Vision Based Analysis and Harvest of Somatic Embryos", Computers and Electronics in Agriculture, vol. 9, 1993, pp. 13-23.
Rodriguez et al., "Mechanical Purification of Torpedo Stage Somatic Embryos of Daucus Carota L.", Plant Cell, Tissue and Organ Culture, vol. 23, 1990, pp. 9-14.
Von Arnold et al., "Spruce Embryogenesis", Methods in Molecular Biology, vol. 427, 2008, pp. 31-47.
Office Action received for European Patent Application No. 09730557.7, mailed on Mar. 25, 2011, 3 pages.
Final Office Action received for U.S. Appl. No. 12/937,240, mailed on Aug. 27, 2012, 5 pages.
Non Final Office Action received for U.S. Appl. No. 12/937,240, mailed on Feb. 23, 2012, 6 pages.
Non Final Office Action received for U.S. Appl. No. 12/937,240, mailed on Jan. 9, 2012, 5 pages.
Notice of Allowance received for U.S. Appl. No. 12/937,240, mailed on Nov. 19, 2012, 7 pages.
Restriction Requirement received for U.S. Appl. No. 12/937,240, mailed on Nov. 1, 2011, 5 pages.
Restriction/Election Requirement received for U.S. Appl. No. 13/761,125, mailed on May 3, 2013, 5 pages.
Non Final Office Action received for U.S. Appl. No. 13/761,125, mailed on Jun. 27, 2013, 7 pages.
Non-Final Office Action received for U.S. Appl. No. 13/761,125, mailed on Jan. 30, 2014, 7 pages.
Final Office Action Received for U.S. Appl. No. 13/761,125, mailed on Jul. 1, 2014, 5 pages.

* cited by examiner

METHOD FOR DISPERSION OF ASSEMBLIES OF BIOLOGICAL MATERIAL

CROSS REFERENCE TO RELATED APPLICATIONS

This is a U.S. National Phase patent application of PCT/SE2010/051083, filed Oct. 7, 2010, which claims priority to Swedish Patent Application No. 0950743-5, filed Oct. 9, 2009, and U.S. Provisional Patent Application No. 61/250,021, filed Oct. 9, 2009, each of which is hereby incorporated by reference in the present disclosure in its entirety.

This invention was made based on a joint research agreement between Georgia Tech Research Corporation and SweTree Technologies AB.

BACKGROUND TO THE INVENTION

When working with assemblies of biological material, such as animal tissue, assemblies of cultured animal cells, plant tissue, assemblies of cultured plant cells or assemblies of plant embryogenic mass, it is commonplace that dispersion of such assemblies is desired.

For instance, when culturing mammalian cells in suspension culture, the cells often adhere to each other forming spherical clusters, dispersion of which is necessary when passaging the culture. Examples of cells forming spherical clusters in suspension culture include HEK293 cells, embryonic stem cells and neuronal stem cells.

Also when initiating a primary cell culture from a tissue sample, gentle dispersion of the tissue is often called for.

Known methods for dispersing assemblies of biological material include enzyme treatments and various mechanical dispersion methods. One dispersion device is disclosed in PCT/US09/39981.

In cases that the recovery of viable cells from the assemblies of biological material is desired, it is especially important that the method of dispersion be sufficiently gentle to not to damage the cells too much. In many cases, it is of interest to be able to control the degree of dispersion.

Thus, it is an object of the invention to provide a device and a method of gentle dispersion of assemblies of biological material, such as animal tissue, assemblies cultured animal cells, plant tissue, assemblies of cultured plant cells or assemblies of plant embryogenic mass. An advantage of the device and the method is that the degree of dispersion is controllable.

SUMMARY OF THE INVENTION

The present invention relates to methods and devices for gently dispersing assemblies of biological material (preferably in vitro cultured biological material) into smaller assemblies of biological material.

In a first aspect, a method of dispersion of assemblies of biological material selected from plant tissue, assemblies of cultured plant cells and assemblies of plant embryogenic mass suspended in a liquid into smaller assemblies of biological material is provided, said method including at least one dispersion sequence, which comprises the following steps:
i) providing a disperser comprising a flow channel (100) arranged in a loop configuration for re-circulation of the assemblies to be dispersed in the flow channel (100), the flow channel (100) including at least one constriction, such that assemblies of biological material flowing through the flow channel (100) are first subjected to axially extensional strain and radially compressional strain, and then to axially compressional strain and radially extensional strain from fluid dynamics forces;
ii) using the disperser to subject the assemblies of biological material to fluid dynamics forces causing axially extensional strain and radially compressional strain;
iii) using the disperser to subject the assemblies of biological material to fluid dynamics forces causing axially compressional strain and radially extensional strain from fluid dynamics forces; and
iv) repeating said steps ii) and iii) in sequence until the assemblies of biological material are dispersed into the desired smaller assemblies of biological material.

In a second aspect, a method of dispersion of assemblies of plant embryogenic mass suspended in a liquid into smaller assemblies of plant embryogenic mass is also provided, said method including at least one dispersion sequence, which comprises the following steps:
i) subjecting the assemblies of plant embryogenic mass to fluid dynamics forces causing axially extensional strain and radially compressional strain;
ii) subjecting the assemblies of plant embryogenic mass to fluid dynamics forces causing axially compressional strain and radially extensional strain from fluid dynamics forces; and
iii) repeating said steps i) and ii) in sequence until the assemblies of plant embryogenic mass are dispersed into the desired smaller assemblies of plant embryogenic mass.

Preferably, the strength of the extensional and compressional strains increases with each repeated sequence. In this manner, the larger assemblies will not encounter too strong dispersive effects but as the assemblies get smaller the dispersive effect needed to achieve dispersion increases. Increasing the dispersive effect stepwise thus allows gentle dispersion into ever smaller assemblies.

Preferably, the methods comprise the step of visually inspecting the degree of dispersion between repetitions of the dispersion steps, and terminating the repetitions when the desired degree of dispersion is achieved. Terminating repetitions at optimal time allows for shortest possible processing time and the least amount of stress to the material dispersed.

Preferably, the desired smaller assemblies have a size in the range of 0.5-2 mm, more preferably 0.7-1.7 mm, 0.8-1.6 mm or 0.8-1.2 mm.

In a third aspect, a disperser for dispersing assemblies of biological material is disclosed, comprising a flow channel (100) including at least one constriction, such that assemblies of biological material flowing through the flow channel (100) are first subjected to axially extensional strain and radially compressional strain, and then to axially compressional strain and radially extensional strain from fluid dynamics forces and wherein the flow channel (100) is arranged in a loop configuration for re-circulation of the assemblies to be dispersed in the flow channel (100).

Preferably the flow channel further comprises a mixing chamber (101) for mixing the assemblies being dispersed between and/or during re-circulations.

Preferably the mixing chamber (101) comprises a transparent wall section for visual inspection of the size distribution of the assemblies being dispersed.

Preferably, the flow channel comprises at least two constrictions, each constriction having an inner diameter, which is equal to or smaller than the inner diameter of the constriction immediately up-stream of thereof.

Preferably, the flow channel includes an intermediate portion having a constant cross-section, between each constriction.

Preferably, each intermediate portion has an inner diameter, which is equal to or smaller than the inner diameter of the intermediate portion immediately up-stream of thereof.

Preferably, each intermediate portion may have a length at least equal to the size of the biological material to be dispersed. Preferably, the length of each intermediate portion is in the interval from 2.5 mm to 60 mm, more preferably from about 5 mm to about 30 mm. The number of constrictions may be 3-100, preferably 5-20, most preferably about 10. Preferably, the constrictions have a cross-sectional area in the interval from 0.75 to 1300 mm$^2$, more preferably in the interval from 3 to 32 mm$^2$.

The flow channel may have axisymmetric cross-section. The flow channel may have an essentially circular or oval cross-section.

At least part of the flow channel may have a non-axisymmetric cross-section such as a rectangular cross-section. The cross-section of each non-axisymmetric constriction, having a maximal dimension, may preferably be oriented such that the maximal dimension of each constriction is rotated, preferably at least 30°, more preferably about 90° in relation to maximal dimension of the next non-axisymmetric constriction in sequence. The cross-section of each constriction may represent a rectangle, having a first and a second side, wherein the first side is longer than the second side, and the constrictions are oriented such that first side of each constriction is perpendicular to the first side of the next constriction in sequence having a rectangular cross-section.

The disperser may preferably comprise means of recirculating the liquid in the flow channel (100). The recirculating means preferably comprise a pump (104), preferably a peristaltic pump.

In a fourth aspect, a method of dispersion of assemblies of biological material is provided, said method including at least one dispersion sequence, which comprises the following steps:
  i) providing a disperser according to the third aspect of the invention;
  ii) using the disperser to subject the assemblies of biological material to fluid dynamics forces causing axially extensional strain and radially compressional strain;
  iii) using the disperser to subject the assemblies of biological material to fluid dynamics forces causing axially compressional strain and radially extensional strain from fluid dynamics forces; and
  iv) repeating steps ii) and iii) in sequence until the assemblies of biological material are dispersed into the desired smaller assemblies of biological material.

The advantages of the methods and the device of dispersion include:
(1) Not requiring moving parts except optionally means of driving the flow through the disperser and therefore being robust
(2) Providing a controllable means of dispersion
(3) Being gentle to the biological material
(4) Being fast
(5) The device being compact and completely enclosed allows easy sterilization.

DEFINITIONS

The term assemblies of biological material comprises all types of assemblies of biological material that may be of interest to disperse. Examples of such assemblies include animal tissue, assemblies cultured animal cells, plant tissue, assemblies of cultured plant cells or assemblies of plant embryogenic mass.

The term plant embryogenic mass refers collectively to the material consisting of immature embryogenic tissue, or embryos and immature embryogenic tissue, present in the liquid or solid culture of somatic embryos.

The term immature embryogenic tissue refers to all material other than embryos that are in the plant embryogenic mass. The term tissue is being used here in an unconventional manner consisting of largely undifferentiated cells and should not to be confused with the normal reference to plant tissue with specialized cells.

The terms embryogenic clusters, embryo clusters or clusters, are used interchangeably. The term refers to assemblies of plant embryogenic mass held together as a continuous solid material of finite size on solid medium or in liquid medium.

The terms somatic embryo, embryo and plant somatic embryo are used interchangeably. The terms refer to plant embryos derived from somatic tissue of a plant.

Norway spruce is a spruce species with the Latin name Picea abies native to Europe.

The terms fluid dynamics and hydrodynamics are used interchangeably and refer to the same physical principles of flow of fluids.

The terms channel and tube are used interchangeably without specific implication to the geometry of the passage unless otherwise stated.

The orthogonal directions in polar coordinates are given by axial, radial and angular (azimuthal) directions. These directions correspond to the central axis of a cylinder which is normal to the circular cross-section of the cylinder, and the radial and angular directions pointing along the radius and normal to the radius on the cross-sectional surface, respectively.

Axisymmetric flow refers to flow inside a tube where the cross-sectional surface of the tube is always circular, and therefore, there is symmetry with respect to the axis of the tube. In other words, nothing changes along the angular (or azimuthal) direction.

Stress is force per unit area.

Strain is the geometrical measure of deformation representing the relative displacement between points in the material body; it is represented as the ratio or percentage of deformation in relation to the original dimension.

Normal strain defines the ratio or percentage amount of stretch or compression along material line elements (ratio of the deformation to the original length in the direction of the deformation).

Shear strain defines the ratio or percentage amount of deformation relative to the original dimension associated with the sliding of material plane layers over each other.

Extensional strain is a normal strain where the element stretches.

Axially extensional strain is an element that stretches along the axial direction.

Radially extensional strain is an element that stretches along the radial direction.

Compressional strain is a normal strain where the element contracts.

Axially compressional strain refers to deformation of an element that contracts along the axial direction.

Radially compressional strain refers to deformation of an element that contracts along the radial direction.

Rate of Stain is the change in strain with respect to time.

Hydraulic diameter, $D_h$, is a term used to characterize flow in noncircular tubes and channels. By definition, it is given by $D_h = 4 A/S$ where A is the cross-sectional area of the noncircular tube or channel and S is the wetted perimeter of the cross-section.

Mean velocity in a channel is defined as the volumetric flow rate divided by the cross-sectional area of the channel.

Contraction ratio is defined as the ratio of the mean velocity at the outlet to the mean velocity at the inlet in a channel.

Mean stress is the stress that is averaged over a surface.

Mean rate of strain is the rate of strain averaged over a surface.

Dynamic viscosity of a fluid is the ratio of shear stress to rate of shear strain in a Newtonian fluid element. Water, glycerin, silicone oil are examples of Newtonian fluids.

Rate of strain profile is a profile showing the variation of the rate of strain.

Unit of length in millimeter is abbreviated as "mm".

Unit of rate of strain as reciprocal second is abbreviated as "1/s".

In general, a flow with higher average rate of strain will impose higher average stress on a particle or on an assembly of particles suspended in the fluid.

TABLE 1

Figure 1:
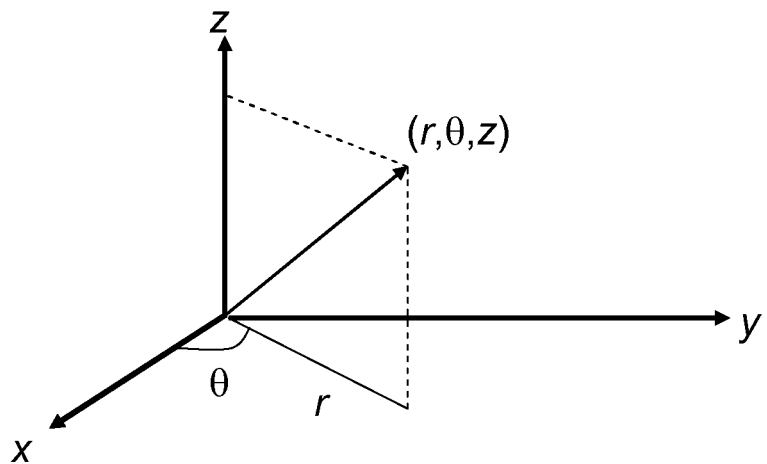
FIG. 1 illustrates the coordinate parameters used in the description.

List of designations pertaining to the FIGURES.

| | |
|---|---|
| 1 | Segment of an axisymmetric flow channel (100) |
| 2 | Segment of an axisymmetric flow channel (100) |
| 3 to 40 | Dimensions according to table 3 |
| 41 | Connector tube |
| 81 | Segment of a non-axisymmetric flow channel (100) |
| 81a | Cross section of 81 |
| 82 | Segment of a non-axisymmetric flow channel (100) |
| 82a | Cross section of 82 |
| 42 to 90 | Dimensions according to table 4 |
| 100 | Flow channel with constriction/s (disperser tube) |
| 101 | Mixing chamber with optional visual inspection opening/window |
| 102 | Inlet |
| 103 | Outlet |
| 104 | Pump, preferably a peristaltic pump |
| 105 | Valve, preferably a three-way valve |
| 106 | Valve, preferably a three-way valve |
| 107 | Fluid reservoir |
| 108 | Connecting tube |

DETAILED DESCRIPTION OF THE INVENTION

Method of Dispersing Assemblies of Biological Material

A method of dispersion of assemblies of biological material (preferably in vitro cultured biological material) suspended in a liquid into smaller assemblies of biological material is disclosed, said method including at least one dispersion sequence, which comprises the following steps:
i) providing a disperser comprising a flow channel (100) arranged in a loop configuration for re-circulation of the assemblies to be dispersed in the flow channel (100), the flow channel including at least one constriction, such that assemblies of biological material flowing through the flow channel are first subjected to axially extensional strain and radially compressional strain, and then to axially compressional strain and radially extensional strain from fluid dynamics forces;
ii) using the disperser to subject the assemblies of biological material to fluid dynamics forces causing axially extensional strain and radially compressional strain;
iii) using the disperser to subject the assemblies of biological material to fluid dynamics forces causing axially compressional strain and radially extensional strain from fluid dynamics forces;
iv) repeating said steps ii) and iii) in sequence until the assemblies of biological material are dispersed into the desired smaller assemblies of biological material.

A method of dispersion of assemblies of plant embryogenic mass suspended in a liquid into smaller assemblies of plant embryogenic mass is also disclosed, said method including at least one dispersion sequence, which comprises the following steps:
i) subjecting the assemblies of plant embryogenic mass to fluid dynamics forces causing axially extensional strain and radially compressional strain;
ii) subjecting the assemblies of plant embryogenic mass to fluid dynamics forces causing axially compressional strain and radially extensional strain from fluid dynamics forces; repeating said steps in sequence until the assemblies of plant embryogenic mass are dispersed into the desired smaller assemblies of plant embryogenic mass.

Preferably, the strength of the extensional and compressional strains increases with each repeated sequence.

Preferably, the method comprises the step of visually inspecting the degree of dispersion between repetitions of the dispersion steps, and terminating the repetitions when the desired degree of dispersion is achieved.

Preferably, the assemblies of biological material are selected from a group consisting of: assemblies in vitro cultured animal cells, plant tissue, assemblies of cultured plant cells and assemblies of plant embryogenic mass.

Preferably, the biological material is assemblies of plant embryogenic mass and the desired smaller assemblies have a size in the range of 0.5-2 mm, more preferably 0.7-1.7 mm, 0.8-1.6 mm or 0.8-1.2 mm.

Device for Dispersing Assemblies of Biological Material

To illustrate the construction of the disperser device, certain possible embodiments are disclosed in detail. The level of detail should not be construed as limiting unless explicitly stated so.

Overall Construction

A disperser device for dispersing assemblies of biological material is provided. The liquid may be any liquid which is not too viscous to flow in the apparatus, and which is benign to the biological material, preferably water, water-based buffer or liquid culture medium.

The disperser device comprises a flow channel (100). The flow channel (100) may be manufactured as a single entity or as two or more parts comprising an individual segment each. The flow channel (100) may for example be constructed of two parts, first segment (1)/(81) and second segment (2)/(82), see FIGS. 2/3, respectively. It may be advantageous to manufacture the device with several individual segments as this will enable the device to be more easily adapted to different starting materials and will simplify cleaning and maintenance.

For example, the disperser flow channel segments (100) may be connected to a mixing chamber (101) containing (during operation) liquid comprising assemblies of biological material. The first segment (100*a*) of the disperser flow channel (100) may be connected to the second segment (100*b*) by a connecting tube (108), in which a pump (104) is arranged. In this example, the dispersed biological material leaves the second segment (100*b*) at the outlet connected to the same mixing chamber (101) thus returning the liquid and the biological material, now more dispersed, to the mixing chamber (101).

The disperser device flow channel (100) comprises at least one constriction, such that assemblies of biological material flowing through the flow channel (100) are first subjected to axially extensional strain and radially compressional strain, and then to axially compressional strain and radially extensional strain from fluid dynamics forces. When the flow channel (100) comprises at least two constrictions, each constriction may have an inner diameter, which is equal to or smaller than the inner diameter of the constriction immediately up-stream of thereof in order to apply effective dispersing forces to the assemblies of biological material. Preferably, the disperser device has a set of constrictions, whereby repeated strain application allows for more effective dispersion. The number of constrictions in a set of constrictions may for example vary from 1 to 100, 1 to 20, from 4 to 16 or 6 to 12, and the preferred number of constrictions is about 10, and depends on the nature of the assemblies to be dispersed. Higher number provides more vigorous dispersing but increases the stress on the biological material to be dispersed.

The flow channel (100) may comprise an intermediate portion having an essentially constant cross-section, between each constriction. Each intermediate portion can have an inner diameter, which is equal to or smaller than the inner diameter of the intermediate portion immediately up-stream of thereof, thereby increasing the dispersing forces step by step.

Preferably, the flow channel(s) (100) have an essentially circular cross-section, except for the constrictions which are subject to special considerations, as described below. Other geometries (such as oval, hexagonal, octagonal, rectangular with rounded corners, or triangular with rounded corners) may be used as long as the biological material does not become damaged during their passage of the flow channel (100) as result of the geometry. Tubes having circular cross-sections are easy to manufacture.

Depending on the type of biological material, it may be preferable that the flow channel(s) (100) are smooth on the inside. Any roughness on the inner surfaces may easily damage certain delicate biological materials and is thus best avoided for these materials. For other types of biological material it may be preferable that the inner surface may have a degree of roughness. In certain cases, this may facilitate dispersion and promote growth and development of the biological material.

Fluid Dynamics Considerations

It is critical to avoid imposing too much hydrodynamic stress which could cause damage to the biological material. On the other hand, the stresses must be sufficient to disperse at least a significant fraction of the assemblies. The optimal levels of stresses for the assemblies of biological material of a particular type, cell line or species to be dispersed may need to be determined experimentally. Once the optimal levels have been determined or obtained, the necessary disperser device parameters may be calculated accordingly. Alternatively, a disperser having minimum and maximum dimensions dictated by the size of the assemblies of biological material to be dispersed and the desired size of dispersed assemblies of biological material, exerting gentle stress may be constructed to determine whether such dispersion is efficient for the assemblies at hand (see below for details). If not, a disperser with more rigorous dispersing activity may be constructed and tested, and the process repeated until a satisfactory result is obtained.

Certain constants are preferably decided upon before calculating the remaining parameters of the disperser design. Dynamic viscosity of the fluid affect the hydrodynamic forces and the intended fluid should be chosen. Preferably, the fluid is essentially water, having well-known dynamic viscosity which can be taken as a constant in a constant temperature environment for the design of a disperser device. The dynamic viscosity of water is not generally significantly affected by small amounts of salts, simple carbohydrates, amino-acids or similar low molecular weight compounds. If the dynamic viscosity of the fluid cannot be obtained from literature, it may be experimentally measured by means known to the skilled person.

Flow rate also affects the hydrodynamic forces. The desired flow rate may in part depend on desired capacity of the disperser device, wherein faster flow may allow higher capacity. For simplicity, the design of the disperser is preferably based on a constant flow rate, which can be taken as another constant for the design of a disperser device. By varying the flow rate, the hydrodynamic forces may then be fine-tuned without having to modify the dimensions of the device.

According to the invention, the inner dimensions of the flow channels vary along the flow direction forming at least one constriction, preferably a set of constrictions. The inner dimensions at these constrictions are a critical parameter, since it is the value of the inner dimensions at the constriction that dictate the magnitude of the extensional and compressive hydrodynamic strains, and it is the said extensional and compressive hydrodynamic strains that impose extensional and compressive stresses on the assemblies of biological material, gently forcing the assemblies to disperse.

According to the invention, the dimensions of the constrictions are selected according to the level of extensional and compressive stress that is required to be imposed on the assemblies of biological material and the size of the assembly and the specific type of assembly to be dispersed, taking into account the previously chosen fluid type and flow rate. Preferably, the inner dimensions of the constrictions decrease sequentially from the largest dimensions at the upstream inlet side of the tube to the smallest diameter at the downstream outlet of the tube. The smallest inner dimensions at the extreme downstream side (at the outlet where the assemblies have been fully dispersed) have to be at least large enough to allow a single assembly to pass without damaging the dispersed assembly of the biological material. A preferred minimum dimension is equal or larger than the broadest part of an assembly of biological material at its desired level of dispersion.

Key Dimensions

Considering the above, several key dimensions need to be considered for the flow channel(s) (100):

I. Inner cross-section dimensions and geometry of constrictions

II. Length of constrictions

III. Inner cross-section dimensions and geometry outside of constrictions

IV. Length of sections outside or between the constrictions

The minimum cross-sectional dimension of the flow channel (100) should be larger than the largest dimension of the largest assembly to be dispersed. The maximum cross-sectional dimension of the flow channel (100) does not have to be larger than the largest dimension of the largest assembly to be dispersed. The intermediate portion (inter-constriction) dimensions of the flow channel (100) do not have to be larger than the largest dimension of the largest assembly to be dispersed.

For illustrative purposes, a cylindrical coordinate system is defined, as illustrated in FIG. 1. The general direction of the flow in a disperser device is in the axial direction designated by axis z. The flow also has radial component of velocity in the direction r as it expands and contracts through the disperser device. The axial, radial and angular (in the direction of θ) components of the fluid velocity are defined as $u_z$, $u_r$, and $u_\theta$, respectively.

The term axisymmetric flow is defined to mean that nothing changes in the angular direction, or more precisely $$\frac{\partial(\bullet)}{\partial\theta}=0$$

where (●) represents any flow variable. The term $$\frac{\partial}{\partial\theta}$$

is the usual symbol used in mathematics to mean partial derivative which measures the rate of change of a dependent variable with respect to the independent variable in the denominator keeping all other independent variables constant. In an axisymmetric embodiment of the disperser device, the flow is axisymmetric and the angular velocity component $u_\theta$ is zero.

The rate of axial strain in flow at the centreline of an axisymmetric tube is defined by $$\frac{\partial u_z}{\partial z},$$

where when this quantity is positive the flow is in extensional strain and when negative flow is in compressional strain. Similarly, the rate of radial strain is measured by $$\frac{\partial u_r}{\partial r}$$

where in general when positive represents radial extension and when negative represents radial compression.

Following the same definition as above for axisymmetric extension and compression, for a non-axisymmetric disperser device, the flow is not axisymmetric, and thereby all components of the rate of strain tensor will be nonzero.

Determining Lengths of Constrictions and Intermediate Portions

The length of different parts of the disperser can be calculated based on various axial profiles for the mean rate of strain, $$\frac{dU}{dz},$$

variation, where U is the symbol for the mean velocity defined as the volumetric flow rate divided by the cross-sectional area of the tube in the r-θ plane. The rate of strain along the flow direction can be constant, vary linearly with z, vary quadratically with z, vary as the rate of strain varies along a channel with 'flat walls', or have other functional dependence on z.

The precise functional dependence and variation of the mean rate of strain on z is not as significant as the actual magnitude of the mean rate of strain. For simplicity, we use the case when the mean rate of strain, B, defined by $$B\equiv\frac{dU}{dz},$$

is a constant. Thus, the length of each section (such as for example i=61, . . . 80 in FIG. 3), symbolized by $L_i$ for the axisymmetric tube can be computed based on the constant mean rate of strain in that section, $B_i$, given by $$L_i=\frac{Q}{\pi B_i}\left[\frac{1}{R_{1,i}^2}-\frac{1}{R_{0,i}^2}\right] \qquad \text{Equation 1}$$

where Q is the volumetric flow rate which is always constant along the channel (based on the principle of conservation of mass), R is the radius of the tube, and the subscripts "0" and "1" associated with the radius R define the inlet and outlet radius of each section, respectively. This relation for length from now on is referred to as Eq. (1). The mean rate of strain $B_i$ can be positive or negative, which means that the assembly experiences a mean rate of extensional strain for positive $B_i$ and a mean rate of compressional strain for negative value of $B_i$. A large number of combinations for the length $L_i$ and the mean rate of strain $B_i$ are possible.

Eq. (1) can be generalized to the non-axisymmetric case by using the concept of the hydraulic radius, $R_h$, for each case, which is defined as one half the hydraulic diameter, or mathematically stated $R_h \equiv D_h/2$ where $D_h$ is the hydraulic diameter as defined above.

The equations to determine the length of the contraction or expansion section based on linear, quadratic or 'flat wall' formulation can also be considered. Such equations can be found in the literature for various types of contractions (for reference, see e.g., Parsheh M., Brown, M., and Aidun, C. K., "Fiber Orientation in a Planar Contraction: Shape Effect" *Int. J. Multiphase Flow,* 32, 1354-1369, 2006.)

The case of linear or quadratic mean rate of strain can be considered if there are limitations for the length of the disperser unit. However, the constant mean rate of strain will be sufficient to disperse the assembly if applied in gradually increasing magnitude of the mean rate of strain.

The length of intermediate portions (inter-constriction parts) of the flow channel is determined based on the size of the assembly to be dispersed and should be at least equal to the largest dimension of any assembly to be dispersed. For example, in the case of Norway spruce somatic embryo cluster matured in laboratory Petri dish, the section of the straight tube needs to be at least 10 mm long since the cluster is about 10 mm in size. For embryo clusters matured in a bioreactor, where the size of the cluster is larger, the tube length and the initial diameter should be adjusted to accommodate the larger size of the cluster. As the clusters become smaller as the dispersion progresses, the length of the intermediate portions may also successively decrease. For instance, the length of the intermediate portions may be about 60 mm (preferably about 30 mm) in the beginning of the disperser flow channel and about 2.5 mm (preferably about 5 mm) at the end of the flow channel.

Determining Cross-Section Dimensions

The mean hydrodynamic stress is proportional to the mean rate of strain through the dynamic viscosity of the fluid, which is preferably water.

The contraction ratio, $CR_i$, is defined as the ratio of the inlet to outlet cross-sectional area or mean velocity, or written in terms of the hydraulic radius, this can be stated as, $$CR_i \equiv \frac{R_{o,i}^2}{R_{1,i}^2}, \qquad \text{Equation 2}$$

since area is proportional to radius squared. This relation from now on is referred to as Eq. (2). Examples of these parameters computed for several cases are shown in Table 1. For Norway spruce embryo clusters, the contraction ratio of 3 corresponding to a mean rate of strain, B of 11 reciprocal second (l/s) for contraction diameter from 9.5 millimeter (mm) to 5.5 mm which is considered to exert gentle extensional and compressional stress on the embryo cluster. Where the contraction ratio of 7 corresponding to a mean rate of strain of 36 (l/s) for contraction diameter from 9.5 mm to 3.5 mm is considered to be a relatively strong extensional and compressional stress. Whenever the flow encounters a converging passage or otherwise referred to as a contraction characterized by the cross-sectional area of the passage decreasing in the flow direction, the flow in general will experience an axial extensional rate of strain and a radial compressional rate of strain. The opposite condition is when the flow encounters a diverging passage or otherwise referred to as a expansion characterized by the cross-sectional area of the passage increasing in the flow direction, the flow in general will experience an axial compressional rate of strain and a radial extensional rate of strain. The terms "axial" and "radial" refer to the spatial directions along the center axis of the tube in general direction of the flow (axial), and along the radius of the tube from center toward the surface of the tube normal to the axial direction (radial). When the assembly enters a contraction, it is elongated in the flow direction. As the assembly leaves a contraction and enters the expansion, it is compressed along the flow and stretched along the radial direction. This repeated elongation and compression through the disperser imposes gentle force on different parts of the biological material relative to each other. For example, when two attached plant embryos in a cluster are entering a contraction, the leading embryo is forced to move faster than the trailing embryo because the fluid surrounding the leading embryo is moving faster downstream than the fluid surrounding the trailing embryo. This action results in a gentle and yet finite pull imposed on one embryo relative to the other encouraging the embryos to separate. On the other hand, when the pair of embryos is entering an expansion, the embryos are pressed toward each other along the axial direction but pulled away from each other in the radial direction further encouraging the embryos to separate.

Axisymmetric Cross-Sections

The flow channel (100) may have essentially axisymmetric cross-section throughout the length. For example, the flow channel (100) may have an essentially circular cross-section.

Non-Axisymmetric Cross-Sections

At least part of the flow channel (100) may have a non-axisymmetric cross-section. A non-axisymmetric disperser device (see e.g. FIG. 3), has a similar interior as the symmetric disperser device with the difference that the interior at the constrictions are not essentially circular.

The interior can be of any non circular cross section form, like oval, hexagonal, octagonal, triangular, elliptical, oval, square or rectangular in cross sections (43*a*), (45*a*), (47*a*), (49*a*), (53*a*), (55*a*), (57*a*), or (59*a*). Even irregularly shaped cross-sections may be used.

Axisymmetric cross-sections and non-axisymmetric cross-sections can be combined in the same disperser.

Preferably, the cross-section of each non-axisymmetric constriction, having a maximal dimension, is oriented such that the maximal dimension of each constriction is rotated, preferably at least 30° C., more preferably about 90° in relation to maximal dimension of the next non-axisymmetric constriction in sequence. Such differentially oriented cross-sections provide more effective dispersing than similarly oriented cross-sections.

Preferably, at least part of the flow channel (100) has a rectangular cross-section. A preferred form of constrictions is a rectangular form with rounded corners.

Preferably, the cross-section of each constriction represents a rectangle, having a first and a second side, wherein the first side is longer and the second side, and the constrictions are oriented such that first side of each constriction is perpendicular to the first side of the next constriction in sequence having a rectangular cross-section. Such rectangular alternating cross-sections provide more effective dispersing than constant cross-sections. The corners of the cross-sections are preferably rounded to minimize stresses to the assemblies.

One way of expressing the size of the cross-sections is their cross-sectional area (perpendicular to the flow direction). The constrictions may have a cross-sectional area in the interval from 0.75 to 1300 $mm^2$, preferably in the interval from 3 to 32 $mm^2$.

Loop Configuration of the Flow Channel

The flow channel (100) of a disperser of the invention is arranged in a loop configuration for re-circulation of the assemblies of biological material in the flow channel (100). The loop arrangement allows for circulating the assemblies through the same constrictions repeatedly thus making it possible to construct a more compact, simpler and cheaper device in comparison to a linear flow channel (100) configuration. Preferably, the flow channel further comprises a mixing chamber (101) with means of mixing the matter to be dispersed between (or during) re-circulations. If the flow itself is not sufficient to effect the mixing, the means of mixing may be achieved e.g. by using a moving (e.g. rotating or oscillating) object in the mixing chamber (101) or by agitating the mixing chamber (101) itself.

Preferably, the mixing chamber (101) comprises a transparent wall section for visual inspection of the size distribution of the matter to be dispersed. Use of the loop configuration together with the mixing chamber (101) where the assemblies being dispersed are visually observable allows for monitoring and controlling the degree of dispersion. When the desired level of dispersion is observed in the mixing chamber (101), the dispersion may be terminated either manually or automatically.

The level of dispersion may be determined by determining the size distribution of the assemblies being dispersed. The size distribution determination may be done visually, preferably by digital image analysis means. For example, the contents of the mixing chamber (101) may be imaged using a digital camera, and the resulting images analyzed by means of computerized image analysis. Such image analysis may be used to determine the size distribution of the assemblies being dispersed. Once the assembly size distribution meets a pre-specified threshold, the dispersion process may be discontinued and the dispersed material recovered for further uses.

The re-circulation may be achieved by means of a pump (104) connected to the flow channel (100), which may be any suitable pump preferably with low head and low volume. The pump (104) inlet and outlet are connected such that operating the pump (104) results in circulation of the liquid in the flow channel (100). The pump should also be of a type that does not damage the biological material being dispersed. An example of a suitable pump is a peristaltic pump, but other suitable pumps are also known in the art. For example, outlet of a first segment of the flow channel (100a) is connected to the inlet of the pump (104), preferably a peristaltic pump, and the inlet of a second segment (100b) is connected to the outlet of the pump (104). The inlet of the first segment (100a) is connected to the mixing chamber (101), and the outlet of the second segment (100b) is also connected to the mixing chamber (101). The assemblies to be dispersed may be fed to the chamber through the inlet (102). The flow may be controlled by using the optional valves (105) and (106), which are preferably three-way valves. Fluid reservoir (107) connected to the valve (105) may be used to provide fluid when needed to move the dispersed assemblies further. The dispersed assemblies may be removed though the outlet (103). See FIG. 4 for an illustration.

Certain Specific Embodiments

Exemplary dimensions for a non-axisymmetric disperser suitable for Norway spruce embryogenic mass are presented in Table 2. Table 2 provides an example of the calculation based on Eq. (1), where the length of each contraction is determined based on a fixed desired rate of strain or the rate of strain is calculated based on a fixed length, $L_i$. The first column in this table is the inlet hydraulic diameter, the second column is the outlet or the contraction hydraulic diameter. The third column is the contraction ratio calculated from Eq. (2). The fourth column is the volumetric flow rate with a typical value of 1000 mm³/s which is equal to 1 milliliter/s. The fifth column is the desired rate of strain of 10 (l/s). The sixth column is the calculated length of the contraction based on the fixed rate of strain in the fifth column, in this case 10 (l/s). The seventh column is the computed mean rate of strain based on the equal length of 10 mm from the following relation derived from Eq. (1)

$$B_i = \frac{Q}{\pi L_i}\left[\frac{1}{R_{1,i}^2} - \frac{1}{R_{0,i}^2}\right]. \quad \text{Equation 3}$$

This relation derived from Eq. (1) will be referred to as Eq. (3) from now on. For example, i=61, . . . 80 for a device of FIG. 3.

TABLE 2

Examples of dimension parameters computed based on the desired mean rate of strain and/or based on a fixed length with hydraulic tube radius also applying to non-axisymmetric section of the disperser

| Tube diameter, $2R_0$ (mm) | Contraction diameter, $2R_1$ (mm) | Contraction ratio, CR as defined above | Volumetric flow rate (mm 3/s) | B; Fixed rate of strain (1/s) | Computed length, L (mm) for Fixed rate of strain equal to 10.0 (1/s) based on Eq. (1) | Computed Mean Rate of strain (1/s) based on Fixed Length of 10 mm based on Eq. (3) |
|---|---|---|---|---|---|---|
| 10.00 | 7.00 | 2.04 | 1000 | 10.00 | 1.3 | 1.33 |
| 10.00 | 5.00 | 4.00 | 1000 | 10.00 | 3.8 | 3.82 |
| 10.00 | 3.00 | 11.11 | 1000 | 10.00 | 12.9 | 12.87 |
| 10.00 | 2.00 | 25.00 | 1000 | 10.00 | 30.6 | 30.56 |
| 10.00 | 1.00 | 100.00 | 1000 | 10.00 | 126.1 | 126.05 |

Without any limitations on the various forms and combinations of the disclosed invention, two specific embodiments, one for the manual and one for the automated disperser system are provided herein, as well as examples of operational results achieved.

TABLE 3

Figure 2:
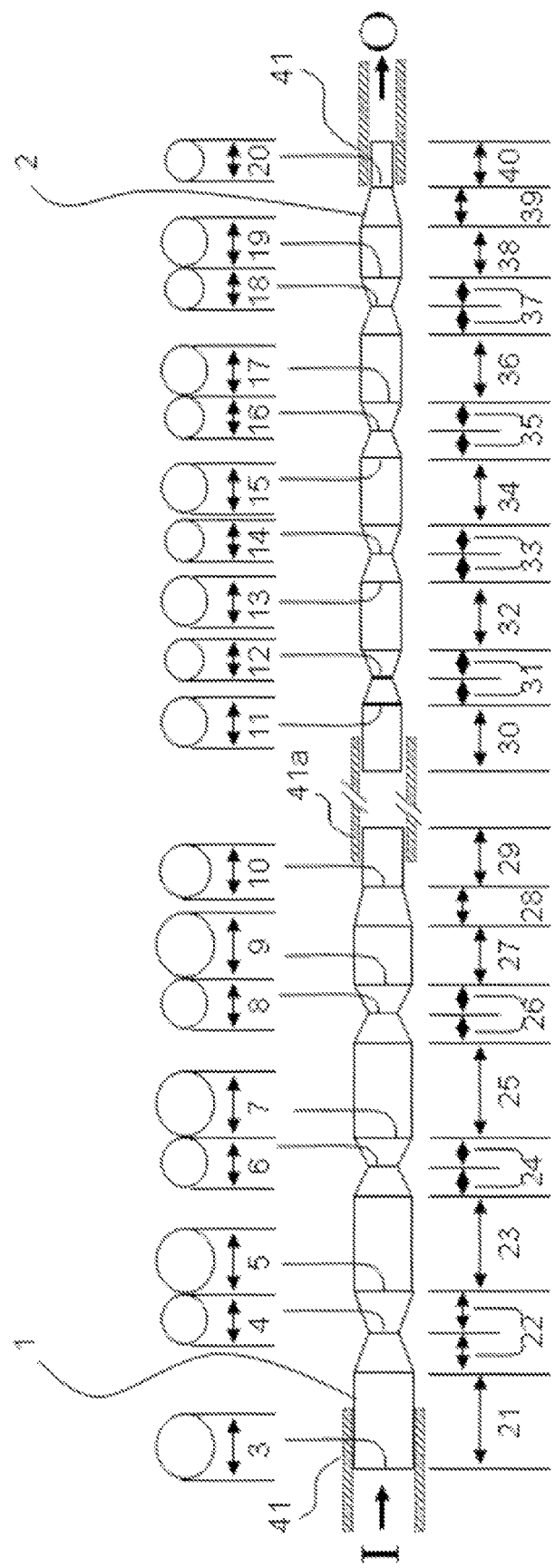
FIG. 2 illustrates details of a device of the invention where the flow channel (100) is axisymmetric.

List of dimension designations pertaining to FIG. 2.

| Cross section position | Inner diameter [mm] | Preferred Inner diameter for Norway Spruce |
|---|---|---|
| (3) | 3.0-10.0 | 9.0-9.5 |
| (4) | 2.0-9.0 | 5.0-5.5 |
| (5) | 3.0-10.0 | 9.0-9.5 |
| (6) | 2.0-9.0 | 4.75-5.0 |
| (7) | 3.0-10.0 | 9.0-9.5 |
| (8) | 2.0-9.0 | 4.0-4.25 |
| (9) | 3.0-10.0 | 9.0-9.5 |
| (10) | 2.0-9.0 | 5.5-6.0 |
| (11) | 2.0-9.0 | 5.75-6.0 |
| (12) | 1.0-8.0 | 3.25-3.5 |
| (13) | 2.0-9.0 | 5.75-6.0 |
| (14) | 1.0-8.0 | 3.0-3.25 |
| (15) | 2.0-9.0 | 5.75-6.0 |
| (16) | 1.0-8.0 | 2.5-2.75 |
| (17) | 2.0-9.0 | 5.75-6.0 |
| (18) | 1.0-8.0 | 2.5-2.75 |
| (19) | 2.0-9.0 | 5.75-6.0 |
| (20) | 2.0-9.0 | 5.75-6.0 |

| Length on details | Length [mm] |
|---|---|
| (21) | 30.0 |
| (22) | 10.0 |
| (23) | 30.0 |
| (24) | 5.0 |
| (25) | 30.0 |
| (26) | 5.0 |
| (27) | 20.0 |
| (28) | 10.0 |
| (29) | 20.0 |
| (30) | 30.0 |

TABLE 3-continued

List of dimension designations pertaining to FIG. 2.

| | |
|---|---|
| (31) | 5.0 |
| (32) | 30.0 |
| (33) | 5.0 |
| (34) | 30.0 |
| (35) | 5.0 |
| (36) | 30.0 |
| (37) | 5.0 |
| (38) | 20.0 |
| (39) | 10.0 |
| (40) | 10.0 |

TABLE 4

Figure 3:
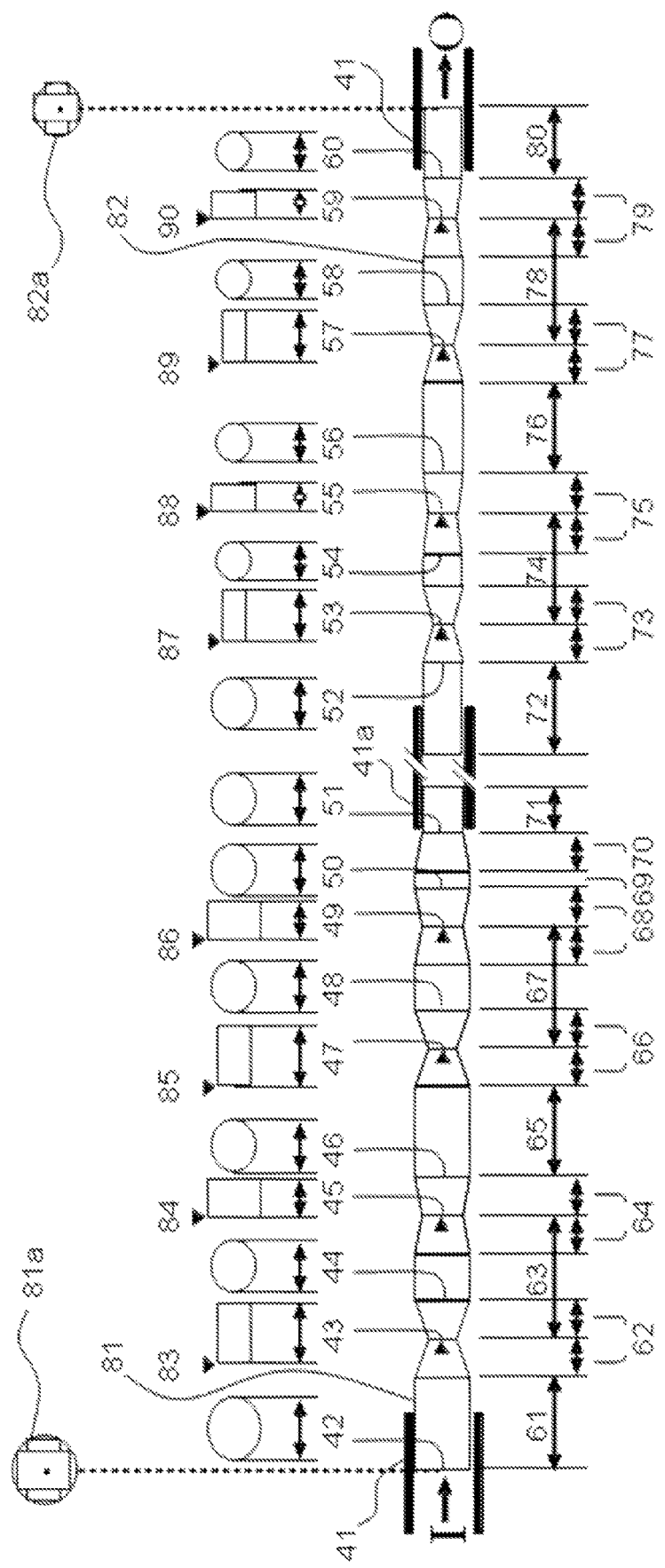
FIG. 3 illustrates details of devices of the invention where parts of the flow channel (100) are non-axisymmetric.

List of dimension designations pertaining to FIG. 3; exemplified inner cross-section dimensions

| | Shape of inner section | Inner dimensions [mm] | | Black arrow side [mm] (83)-(90) | | Width side [mm] | |
|---|---|---|---|---|---|---|---|
| | | Alt. 1 | Alt. 2 | Alt. 1 | Alt. 2 | Alt. 1 | Alt. 2 |
| (42) | circular | 9.5 | 9.5 | | | | |
| (43) | Rectangular | | | (83) 5.0 | (83) 4.75 | 9.5 | 9.5 |
| (44) | circular | 9.5 | 9.5 | | | | |
| (45) | Rectangular | | | (84) 9.5 | (84) 9.5 | 5.0 | 4.25 |
| (46) | circular | 9.5 | 9.5 | | | | |
| (47) | Rectangular | | | (85) 5.0 | (85) 3.75 | 9.5 | 9.5 |
| (48) | circular | 9.5 | 9.5 | | | | |
| (49) | Rectangular | | | (86) 9.5 | (86) 9.5 | 5.0 | 3.5 |
| (50) | circular | 9.5 | 9.5 | | | | |
| (51) | circular | 6.0 | 6.0 | | | | |
| (52) | circular | 6.0 | 6.0 | | | | |
| (53) | Rectangular | | | (87) 3.5 | (87) 3.25 | 6.0 | 6.0 |
| (54) | circular | 6.0 | 6.0 | | | | |
| (55) | Rectangular | | | (88) 6.0 | (88) 6.0 | 3.5 | 3.25 |
| (56) | circular | 6.0 | 6.0 | | | | |
| (57) | Rectangular | | | (89) 3.5 | (89) 2.75 | 6.0 | 6.0 |
| (58) | circular | 6.0 | 6.0 | | | | |
| (59) | Rectangular | | | (90) 6.0 | (90) 6.0 | 3.5 | 2.75 |
| (60) | circular | 6.0 | 6.0 | | | | |

The examples below should be construed as non-limiting.

EXAMPLES

Example 1

Manual Disperser

One of the disperser systems built according to the invention (Manual Disperser) comprises of two glass disperser tubes one with 9 mm inside diameter (tube A), and the other with 6 mm inside diameter (tube B). Tube A has 3 axisymmetric constrictions each with 5 mm inside diameter. Tube B has 4 non-axisymmateric constrictions all with substantially rectangular cross-sections with internal sides equal to 3.5 mm and 4.5 mm with each subsequent rectangular constriction oriented with a 90 degree angle relative to the immediate neighboring constriction. The outlet of glass tube A is attached with flexible autoclavable plastic (TYGON 3350 Silicone) tubes to the inlet of glass tube B. The outlet of glass tube B is attached with an autoclavable plastic tube to special autoclavable rubber tubing at the peristaltic pump and to another glass tube (tube C) with 6 mm internal diameter with a cylindrical reservoir 20 mm in inside diameter and 55 mm length followed by two axisymmetric constrictions with 4 mm inside diameter followed by 3 mm inside diameter.

The reservoir provides the means to closely and clearly observe and inspect the clusters downstream of the disperser tubes A and B, and to decide whether the clusters are small enough. If the clusters are not small enough, then the operator can allow the clusters to pass through the disperser tubes for another pass until satisfactory size is achieved.

Example 2

Automated Disperser

Figure 4:
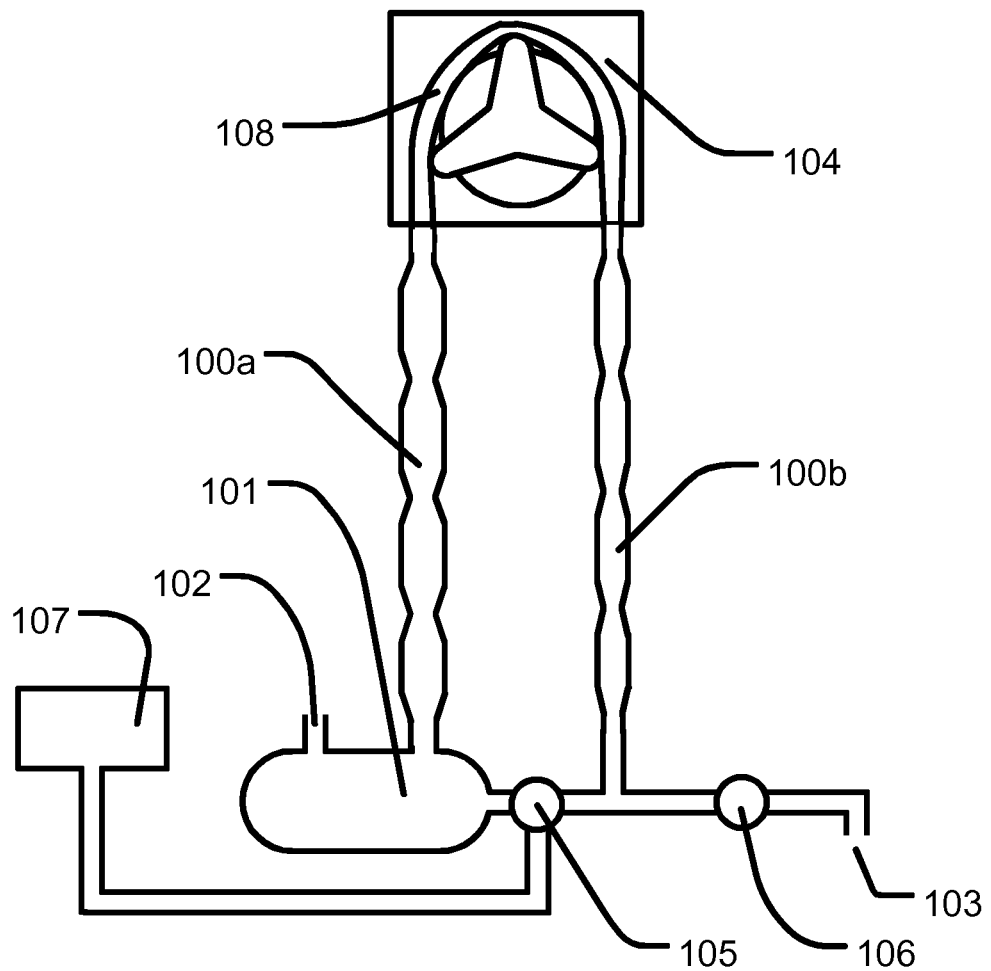
FIG. 4 illustrates an embodiments of an automatic dispersion device of the invention.

In one embodiment of the invention, the system is automated (Automated Disperser) with two disperser tubes (100a and 100b) each with four (4) constriction regions attached at one end to a peristaltic pump (104) and with the other end attached to a flow loop, as shown in FIG. 4. The flow loop consists of a mixing-visualization chamber (101) 10 mm wide (in direction normal to the plane of view), 50 mm long and 40 mm tall. The mixing and visualization chamber (101) has a dual purpose. It is (a) used to continuously keep the assemblies of biological material dispersed and mixed, if necessary with a magnetic stirrer placed under the chamber, and (b) used to inspect the size of the assemblies using digital video imaging and image analysis software for size distribution (for example see http://www.smartimtech.com/analysis/images/sc_r21_2big.jpg). Once the size distribution of the assemblies reduces below a set threshold, the assemblies will be guided further, such as onto a bioreactor or a petri plate, as the process requires. The components and operational steps of the device are described herein.

Initially, the embryogenic clusters will be introduced into the mixing-visualization chamber while the three-way solenoid valves 105 and two-way solenoid valve 106 are closed, and the Peristaltic pump is off, as shown schematically in FIG. 4. The inlet tube 102 of the mixing and visualization chamber is then plugged and the solenoid valve, 105 is opened to flow from disperser tube 1 to mixing and visualization chamber. The speed of the pump is adjusted to keep the assemblies continuously dispersed in the chamber. If the flow requires further agitation to keep the assemblies dispersed, then a magnetic stirrer can be placed in the mixing chamber. The image analysis system is used to monitor the size distribution of the assemblies while the clusters pass through the disperser tubes and separate into the smaller size assemblies. The volume of the assemblies to the liquid medium should not be more than 5% for best automated visualization and image analysis results. However, in practice volume ratios of up to 10% can be processed, although the larger the ratio the more inaccurate the results due to interaction of the assemblies and overlap of the assemblies in the image. Once the image analysis system reports a size distribution that is acceptable, such as clusters of 1 mm or less in the case of the Norway Spruce, the solenoid valve 106 will open and 105 will be closed and the dispersed material exits through the outlet 103.

Example 3

Growth and Development of Somatic Embryos of Norway Spruce in a Temporary Immersion Bioreactor System Small clusters of embryogenic masses of Norway Spruce (cell line 06:28:05, 06:04:12, 04:45:34) processed with the dispersion device described herein (Example 1), were transferred into the temporary immersion bioreactor system by means of a 50 ml pipettes and dispersed evenly on the bottom screen for proliferations of immature embryogenic tissue. Prior to transferring the dispersed somatic embryo clusters, culture medium supporting proliferation of the somatic embryos, being 1/2LP supplemented with 2,4 D and BA, had been applied for proliferation of the somatic embryos. After two to three weeks in proliferation medium depending on cell line, (a) the proliferating culture were re-dispersed according to the method outlined in Example 3 below; or (b) the medium was changed to pre-maturation medium, e.g. DKM, or (c) maturation medium, e.g. DKM supplemented with ABA. After treatment (b) and (c), or (c) alone, four to six weeks later a dense number of mature embryos was observed on the surface of the bioreactor screen. The embryos matured substantially more uniformly as the case without application of dispersion with notable difference. In the case of dispersed small clusters being the starting material for proliferation in the bioreactor, on average there were ten to 20 number of substantially uniform mature embryos per square centimeter of the screen surface area. In the case of non-dispersed clusters in the temporary immersion bioreactor, the embryos appear on the surface of a substantially spherical large cluster of embryogenic mass. The diameter of the non-dispersed cluster is about 20 mm or larger. On average, there were 15 embryos on the surface of a large spherical cluster with a substantially non-uniform stage of development showing a broad distribution in size variation. In cultures of somatic embryos cultured on solid medium of the same composition as used herein, i.e. DKM with ABA, the yield and quality of mature somatic embryos are comparable to the non-dispersed cultures in the temporary immersion bioreactor.

Example 4

Dispersion of Clusters of Embryogenic Masses of Norway Spruce Cultured on Solid Medium The two ends of tubes A and C of the manual disperser tubes were immersed in liquid medium inside disperser vessel. The entire system was sterilized in an autoclave and the process described herein took place under the hood. Several clusters of embryogenic masses of Norway Spruce (cell line 06:28:05, 06:04:12, 04:45:34) with average hydraulic diameter of the cross-section taken from the mid-section of the cluster ranging from 5 mm to 10 mm were collected from the surface of solid culture medium by forceps into the said disperser vessel of the invention described above (Example 1). The largest original embryogenic masses in culture with about 10 mm or larger in diameter were broken down into smaller clusters by tearing apart by forceps. Beyond about 5 mm in size, it was very difficult to further breakup with forceps. A volume of liquid culture medium of the same composition as the solid medium from which the clusters were collected were added to the disperser vessel before adding the clusters. The clusters in the liquid culture medium in the disperser vessel were collected into the first disperser tube by manually directing the rod over the clusters and passed through the disperser tube 1 through pressure gradient imposed by a peristaltic pump connected to the loop. It was observed consistently that as the clusters passed through the first disperser tube and left the second disperser tube, the clusters leaving the second disperser tube were much smaller than the original clusters entering the first disperser tube. The small clusters created by the compressions and extensions created by the constrictions in the disperser tubes are released from the second disperser tube of the disperser vessel. The clusters passing through the disperser tubes once were collected and measured. It was found that the clusters that had passed through the disperser tubes once had a diameter that ranged from hydraulic diameter of the cross-section of the cluster ranging from 0.5 mm to 2 mm. Upon subsequent passes, the clusters would further breakup into smaller clusters but at a slower rate. It was observed that it is easier to breakup larger clusters compared to smaller ones. That is the smaller the cluster, the more passes it required to breakup. This is understandable as the cluster size becomes much smaller than the constrictions, then the effect of the extensional and compressional strain will be less consequential.

The small clusters of cells were dispersed evenly on the screen of a partially immersed bioreactor for further proliferation and maturation. The medium 1/2LP or DKM supplemented with 2,4 D and BA was applied for proliferation, or for pre-maturation treatment, of the somatic embryos. After two to three weeks in proliferation medium depending on cell line, the medium was changed to pre-maturation medium DKM, or maturation medium DKM supplemented with ABA. Four to six weeks later a dense number of mature embryos were observed on the surface of the bioreactor screen. The embryos matured substantially more uniformly as the case without application of dispersion with notable difference. In the case of dispersed small cell clusters being the starting material for proliferation in the bioreactor, on average there were ten to 20 number of substantially uniform mature embryos per square centimeter of the screen surface area. In the case of non-dispersed clusters, the embryos appear on the surface of a substantially spherical large cluster of embryogenic mass. The diameter of the nondispersed cluster is about 20 mm or larger. On average, there were 15 embryos on the surface of a large spherical cluster with a substantially non-uniform stage of development showing a broad distribution in size variation.

Example 5

Dispersion of Norway Spruce Embryogenic Masses of Norway Spruce Cultured in Temporary Immersion Bioreactors A continuous sheet of embryogenic masses of Norway Spruce (cell line 04:45:34) on top of the nylon screen of a temporary immersion bioreactor system were submerged in liquid culture medium. The sheet was broken up by manually directing the first disperser tube (Example 1) into the sheet to break it up into smaller clusters. The clusters were collected by the first disperser tube and passed through the disperser device (Example 1). by pressure gradient imposed by the peristaltic pump connected to the loop. Smaller parts of the clusters created by the compressions and extensions being the key function of the invention are released from the second disperser tube. Repeated collections of clusters from the disperser vessel and passing through the disperser tubes resulted in a gradually decreased average hydraulic diameter of the cross-section of the clusters to about 1 mm with about 50% variation in cluster size. The dispersed clusters were collected by a 50 ml pipette and transferred to a new bioreactor container for proliferation of a new bioreactor culture.

The invention claimed is:

1. A method of dispersion of assemblies of biological material selected from plant tissue, assemblies of cultured plant cells and assemblies of plant embryogenic mass suspended in a liquid into smaller assemblies of biological material, said method including at least one dispersion sequence, which comprises the following steps:
   i) providing a disperser comprising a flow channel arranged in a loop configuration for re-circulation of the assemblies to be dispersed in the flow channel, the flow channel including at least two constrictions wherein longitudinal axes of said at least two constrictions align with each other, such that assemblies of biological material flowing through the flow channel are first subjected to axially extensional strain and radially compressional strain, and then to axially compressional strain and radially extensional strain from fluid dynamics forces;

ii) using the disperser to subject the assemblies of biological material to fluid dynamics forces causing axially extensional strain and radially compressional strain;

iii) using the disperser to subject the assemblies of biological material to fluid dynamics forces causing axially compressional strain and radially extensional strain from fluid dynamics forces; and iv) repeating steps ii) and iii) in sequence until the assemblies of biological material are dispersed into smaller assemblies of biological material.

2. A method of dispersion of assemblies of plant embryogenic mass suspended in a liquid into smaller assemblies of plant embryogenic mass, said method including at least one dispersion sequence, which comprises the following steps:

i) subjecting the assemblies of plant embryogenic mass to fluid dynamics forces causing axially extensional strain and radially compressional strain;

ii) subjecting the assemblies of plant embryogenic mass to fluid dynamics forces causing axially compressional strain and radially extensional strain from fluid dynamics forces; and iii) repeating said steps i) and ii) in sequence until the assemblies of plant embryogenic mass are dispersed into the desired smaller assemblies of plant embryogenic mass.

3. The method of claim 1, wherein the strength of the extensional and compressional strains increases with each repeated sequence.

4. The method of claim 1, wherein the method comprises the step of visually inspecting the degree of dispersion between repetitions of the dispersion steps, and terminating the repetitions when the desired degree of dispersion is achieved.

5. The method of claim 1, wherein the smaller size is in the range of 0.5-2 mm.

* * * * *

UNITED STATES PATENT AND TRADEMARK OFFICE
CERTIFICATE OF CORRECTION

PATENT NO. : 8,927,287 B2
APPLICATION NO. : 13/500904
DATED : January 6, 2015
INVENTOR(S) : Cyrus K. Aidun et al.

It is certified that error appears in the above-identified patent and that said Letters Patent is hereby corrected as shown below:

On the title page item (73) Assignee:

Please add --SweTree Technologies AB, Umeå, Sweden--

Signed and Sealed this
Sixteenth Day of June, 2015

Michelle K. Lee
*Director of the United States Patent and Trademark Office*